United States Patent
Halperin et al.

(10) Patent No.: US 8,147,433 B2
(45) Date of Patent: *Apr. 3, 2012

(54) CPR CHEST COMPRESSION MONITOR AND METHOD OF USE

(75) Inventors: Henry R. Halperin, Baltimore, MD (US); Ronald D. Berger, Baltimore, MD (US)

(73) Assignee: Johns Hopkins University, Baltimore, MD (US)

( * ) Notice: Subject to any disclaimer, the term of this patent is extended or adjusted under 35 U.S.C. 154(b) by 1409 days.

This patent is subject to a terminal disclaimer.

(21) Appl. No.: 11/676,152

(22) Filed: Feb. 16, 2007

(65) Prior Publication Data

US 2007/0135739 A1    Jun. 14, 2007

Related U.S. Application Data

(60) Continuation of application No. 11/456,841, filed on Jul. 11, 2006, now Pat. No. 7,429,250, which is a continuation of application No. 09/952,866, filed on Sep. 12, 2001, now Pat. No. 7,074,199, which is a division of application No. 09/188,211, filed on Nov. 9, 1998, now Pat. No. 6,390,996.

(51) Int. Cl.
*A61H 31/00* (2006.01)

(52) U.S. Cl. ........................................................ 601/41

(58) Field of Classification Search .............. 601/41–44, 601/104, 134; 73/379.01, 862.542, 379.03, 73/379.08; 600/594, 587; 434/262, 265
See application file for complete search history.

(56) References Cited

U.S. PATENT DOCUMENTS

| 443,204 A | 12/1890 | Davis | |
|---|---|---|---|
| 651,962 A | 6/1900 | Boghean | |
| 2,071,215 A | 2/1937 | Petersen | 128/28 |
| 2,486,667 A | 11/1949 | Meister | 128/28 |
| RE26,511 E | 12/1968 | Hewson | 128/145.8 |
| 4,424,806 A | 1/1984 | Newman et al. | 128/28 |
| 4,554,910 A | 11/1985 | Lally | 128/28 |
| 4,676,232 A | 6/1987 | Olsson et al. | 128/28 |
| 4,770,164 A | 9/1988 | Lach et al. | 128/28 |
| 4,928,674 A | 5/1990 | Halperin et al. | 128/30.2 |
| 4,932,879 A | 6/1990 | Ingenito et al. | 434/262 |
| 4,987,783 A | 1/1991 | D'Antonio et al. | 73/862.64 |
| 4,989,611 A | 2/1991 | Zanetti | 125/695 |
| 5,453,081 A | 9/1995 | Hansen | 601/150 |

(Continued)

FOREIGN PATENT DOCUMENTS

JP   3030158 A   2/1991

OTHER PUBLICATIONS

Pinchak, et al., Chest Wall Acceleration and Force Measuremen in Simulated and Mechanical CPR, 16 Critical Care Medicine 151 (1988).

(Continued)

*Primary Examiner* — Fenn Mathew

(74) *Attorney, Agent, or Firm* — K. David Crockett, Esq.; Crockett & Crockett, PC

(57) ABSTRACT

A chest compressions monitor for measuring the depth of chest compressions achieved during CPR. A displacement detector produces a displacement indicative signal indicative of the displacement of the CPR recipient's chest toward the recipient's spine. A signaling mechanism provides chest compression indication signals directing a chest compression force being applied to the chest and a frequency of such compressions.

20 Claims, 12 Drawing Sheets

U.S. PATENT DOCUMENTS

| | | | |
|---|---|---|---|
| 5,490,820 A | 2/1996 | Schock et al. | 601/41 |
| 5,496,257 A | 3/1996 | Kelly | 601/41 |
| 5,738,637 A | 4/1998 | Kelly et al. | 601/41 |
| 5,743,864 A | 4/1998 | Baldwin, II | 601/41 |
| 5,831,164 A | 11/1998 | Reddi | 73/514.01 |
| 5,844,482 A | 12/1998 | Guthrie et al. | 340/568 |
| 6,013,041 A | 1/2000 | Leathers | 601/107 |
| 6,027,452 A | 2/2000 | Flaherty et al. | 600/485 |
| 6,174,295 B1 | 1/2001 | Cantrell et al. | 601/41 |
| 6,301,964 B1 | 10/2001 | Fyfe et al. | 73/510 |
| 7,074,199 B2 * | 7/2006 | Halperin et al. | 601/41 |
| 7,108,665 B2 * | 9/2006 | Halperin et al. | 601/41 |
| 7,429,250 B2 * | 9/2008 | Halperin et al. | 601/41 |

OTHER PUBLICATIONS

Gruben, et al., *System for Mechanical Measurements During Cardiopulmonary Resuscitation In Humans*, 37 IEEE Trans. on Biomedical Eng. 204(Feb. 1990).

Pinchak, et al., Accelerometer Measurements in CPR, 37$^{th}$ ACEMB 32 (1984).

* cited by examiner

CPR CHEST COMPRESSION MONITOR AND METHOD OF USE

This application a continuation application of U.S. application Ser. No. 11/456,841, filed Jul. 11, 2006 now U.S. Pat. No. 7,429,250, which is a continuation of U.S. application Ser. No. 09/952,866 filed Sep. 12, 2001, now U.S. Pat. No. 7,074,199, which is a divisional application of U.S. application Ser. No. 09/188,211, filed on Nov. 9, 1998, now U.S. Pat. No. 6,390,996.

BACKGROUND OF THE INVENTION

1. Field of the Invention

The present invention relates to a device for aiding in the administration of cardiopulmonary resuscitation (CPR). More specifically, certain aspects of the invention relate to devices for monitoring CPR efforts and facilitating better CPR administration.

2. Description of Related Art

Various U.S. patent documents disclose sensors for assisting in the administration of CPR. For example, U.S. Pat. No. 5,589,639 (D'Antonio et al.) discloses a force sensing system for a CPR device which generates an intelligible output signal corresponding to a force parameter. The CPR device utilizes a signal indicative of the force being applied to the recipient's chest.

U.S. Pat. No. 5,496,257 (Kelly) discloses an apparatus for assisting in the application of CPR. The device rests on the recipient's chest. Chest compression forces are monitored by the device in order to ascertain the rate of compression and blood flow. This information is actively provided to the rescuer to prompt proper administration of CPR.

Various devices are disclosed which assist in the timing of the application of CPR, including U.S. Pat. No. 5,626,618 (Ward et al.) and U.S. Pat. No. 4,863,385 (Pierce). The '618 patent discloses, among other things, an electrode combination for cardiac pacing and cardiac monitoring in association with a bladder for use in the patient's esophagus for improving artificial circulation as a result of CPR. The '385 patent discloses a CPR sequencer which comprises a compact, portable, computer-controlled device, which provides timing and sequence guidance for helping a rescuer in the application of CPR to a recipient.

Each year there are more than 300,000 victims of cardiac arrest. Current conventional techniques for CPR introduced in 1960 have had limited success both inside and outside of the hospital, with only about 15% survival rate. Accordingly, the importance of improving resuscitation techniques cannot be overestimated. In the majority of cardiac arrests, the arrest is due to ventricular fibrillation, which causes the heart to immediately stop pumping blood. To treat ventricular fibrillation, defibrillation is administered which involves the delivery of a high energy electric shock to the thorax to depolarize the myocardium, and to allow a perusing rhythm to restart. If, however, more than a few minutes pass between the onset of ventricular fibrillation and the delivery of the first defibrillation shock, the heart may be so deprived of metabolic substrates that defibrillation is unsuccessful.

The role of CPR is to restore the flow of oxygenated blood to the heart, which may allow defibrillation to occur. A further role of CPR is to restore the flow of oxygenated blood to the brain, which may prevent brain damage until the heart can be restarted. Thus, CPR is critical in the treatment of a large number of patients who fail initial defibrillation, or who are not candidates for defibrillation.

Various studies show a strong correlation between restarting the heart and higher levels of coronary blood flow. To restart the heart, if initial defibrillation fails (or is not indicated), coronary flow must be provided. With well-performed CPR, together with the use of epinephrine, brain blood flow probably reaches 30-50% of normal. Myocardial blood flow is much more limited, however, in the range of 5-20% of normal. In patients, heart restarting has been shown to correlate with the pressure gradient between the aorta and the right atrium, obtained between compressions (i.e., the coronary perfusion pressure). CPR, when applied correctly, is designed to provide a sufficient amount of coronary perfusion pressure by applying a sufficient amount of chest compression force. Unfortunately, however, studies indicate that CPR is performed correctly only part of the time—approximately 50% of the time according to a study conducted on 885 patients. Hoeyweghen et al., "Quality and Efficacy of Bystander CPR," Resuscitation 26 (1993), pp. 47-52. The same study showed that long-term survival, defined as being awake 14 days after CPR, was 16% in patients with correct CPR, but only 4% when CPR was performed with less chest compression ($p<0.05$). Thus, properly administered CPR can increase survival rates.

Not only is the correct application of CPR critical to the survival of the CPR recipient, but when initial defibrillation is unsuccessful, or is not indicated, it can be essential that CPR be applied immediately. The sooner persons are resuscitated, the more likely they will survive long-term with preservation of neurologic function. When initial resuscitative efforts at the scene of an arrest fail to restore native cardiac function, it is often the practice to transport the patient to the hospital with the hope that better CPR can be performed under the supervision of a physician. A number of studies have shown, however, that it is quite rare for a patient who is not resuscitated in the field to be resuscitated in the hospital, and survive with meaningful neurologic function. Even invasive interventions used in hospitals, such as open chest cardiac massage, have failed to improve survival rates, probably due to irreversible organ damage produced by prolonged schema during transportation.

The American Heart Association (AHA) published guidelines specify that chest compression during CPR should be done at a rate of 80-100 compressions per minute at a depth of 1.5 to 2 inches. During CPR courses, instrumented mannequins are generally used that measure the amount of chest compression a student applies. It is then up to the student to apply similar chest compressions in an emergency situation, without feedback, relying only on the feel and look of the compressions. Since there is no feedback, and since relatively small changes in the amount of compression can affect perfusion pressure, it is not surprising that CPR is often performed incorrectly.

As described above, various types of devices have been provided to help give the rescuer administering CPR feedback. However, these devices do not measure chest displacement. Rather, they measure compression force as a result of the applied CPR. This is problematic since with clinical CPR there is considerable variation in the compliance of different patients' chests, such that similar compression forces produce substantially different chest displacements in different patients.

Gruben et al. disclose in their article entitled "Sternal Force-Displacement Relationship During Cardiopulmonary Resuscitation," Journal of Biomedical Engineering, Volume 115 (May 1993), p. 195, the use of mechanical linkages incorporating position-sensing transducers to measure chest displacement during clinical CPR. However, this mechanism presents problems in general clinical environments, such as delays in setup and awkward handling.

While resuscitation is in progress, it is vital that physicians, paramedics, and other healthcare professionals administering CPR be continuously aware of changes in the patient's electrocardiogram (ECG), particularly the heart rhythm. An incorrect assessment of the heart rhythm can lead to administration of inappropriate therapy or withholding of appropriate therapy. The chest compressions associated with CPR, however, introduce artifacts in the measured ECG signal that make its interpretation difficult. The rather inadequate approach generally used to facilitate ECG interpretation during CPR is intermittent cessation of chest compressions to provide a period of artifact-free ECG acquisition. Problems occur with this approach. For one, there is a loss of hemodynamic support when chest compressions are stopped. In addition, the ECG remains difficult or impossible to interpret once chest compressions are resumed. Accordingly, sudden changes in rhythm may not be appreciated until after a substantial delay. In addition, since survival from cardiac arrest has been shown to be related to blood flow generated during CPR, and since interruption of chest compressions will reduce blood flow, survival may very well be compromised by these interruptions.

The outcome of CPR may be improved if there were a means for reducing the CPR-induced artifacts present in an ECG signal in a manner which would allow the correct interpretation of the ECG without interrupting chest compressions applied during CPR. E. Witherow has performed studies which demonstrate that CPR-induced artifacts are due primarily to changes in the half-cell potential of electrodes, caused by their mechanical disturbance. This was published in a thesis entitled A Study of the Noise in the ECG During CPR, M.S. thesis, the Johns Hopkins University (1993), the content of which is hereby expressly incorporated by reference herein in its entirety.

There is a need for compact, portable, and economic tools for monitoring CPR efforts, aiding in the correct administration of CPR, and otherwise increasing the success of resuscitation efforts, e.g., by removing CPR-induced artifacts from ECG signals so CPR does not need to be stopped in order to obtain a good ECG reading.

SUMMARY OF THE INVENTION

The present invention is provided to aid in the proper application of CPR in various situations in order to substantially improve the survival rate of CPR recipients. The present invention is also provided to improve upon resuscitation techniques involving the concurrent administering of CPR and monitoring of the patient's ECG, and more particularly, the patient's heart rhythm. In order to achieve this end, one or more aspects of the present invention may be followed in order to bring about one or more specific objects and advantages, such as those noted below.

One object of the present invention is to provide a system or device for measuring and prompting chest compressions to facilitate the effective administration of CPR.

A further object is to provide a hand-held CPR chest compression monitor which accurately measures the rate and depth of chest compressions during the administration of CPR. In accordance with one aspect of the invention, the device signals the rescuer to prompt correct compressions. An object of the present invention is to provide such a device which only requires a minimum amount of set-up time, is intuitive in its operation, and is easy to use. The device would preferably be small in size, have a low weight, and be inexpensive to manufacture and distribute.

In accordance with another aspect of the present invention, a hand-held CPR chest compression monitor is provided with an integral defibrillator and/or data storage and retrieval components. Another object of the present invention is to provide a system for concurrently administering CPR with the aid of a hand-held CPR chest compression monitor and obtaining ECG signals from the CPR recipient, and to provide a device for removing compression-induced artifacts found in the ECG signals during CPR to allow accurate ECG and heart rhythm readings without stopping CPR.

The present invention, in accordance with one aspect, is therefore directed to a system (which may be in the form of a hand-held device), for measuring and prompting chest compressions to facilitate the effective administration of CPR by a rescuer. The system comprises a displacement detector for producing an output signal indicative of a displacement of a CPR recipient's chest toward the CPR recipient's spine. A signaling mechanism is provided for providing signals directing a chest compression force being applied to the chest and a frequency of compressions to bring and maintain the frequency of compressions within desired frequency range and to bring and maintain the chest displacement within a desired distance range.

In accordance with an aspect of the invention, the displacement detector comprises a motion detector for determining an amount of motion of the chest in relation to the spine. A converter may be provided for converting an output signal produced by the motion detector into a distance value. The signaling mechanism may comprise a mechanism for comparing the distance value to a desired range of distance values, and for signaling directions regarding chest compression force and frequency in accordance with whether the value falls within the desired range of distance values.

A hand-held CPR chest compression monitor such as that provided above may be used in association with an automated chest compression mechanism to control the manner in which the automated chest compression mechanism applies chest compressions to a recipient to thereby effectively administer CPR to the recipient in accordance with certain chest displacement and compression frequency parameters. Such a hand-held CPR chest compression monitor may be further provided in association with an ECG monitor. An ECG signal enhancer may be provided for subtracting or otherwise suppressing chest compression-induced artifacts from the ECG signal, to facilitate reading of the ECG signal, and more particularly, to facilitate reading of the heart rhythm of the CPR recipient without the need to stop CPR.

BRIEF DESCRIPTION OF THE DRAWINGS

The above and other objects, features, and advantages of the present invention are further described in the detailed description which follows, with reference to the drawings by way of non-limiting exemplary embodiments of the present invention, wherein like reference numerals represent similar parts of the present invention throughout the several views and wherein.

DETAILED DESCRIPTION OF THE PRESENTLY PREFERRED EXEMPLARY EMBODIMENTS

Figure 1:
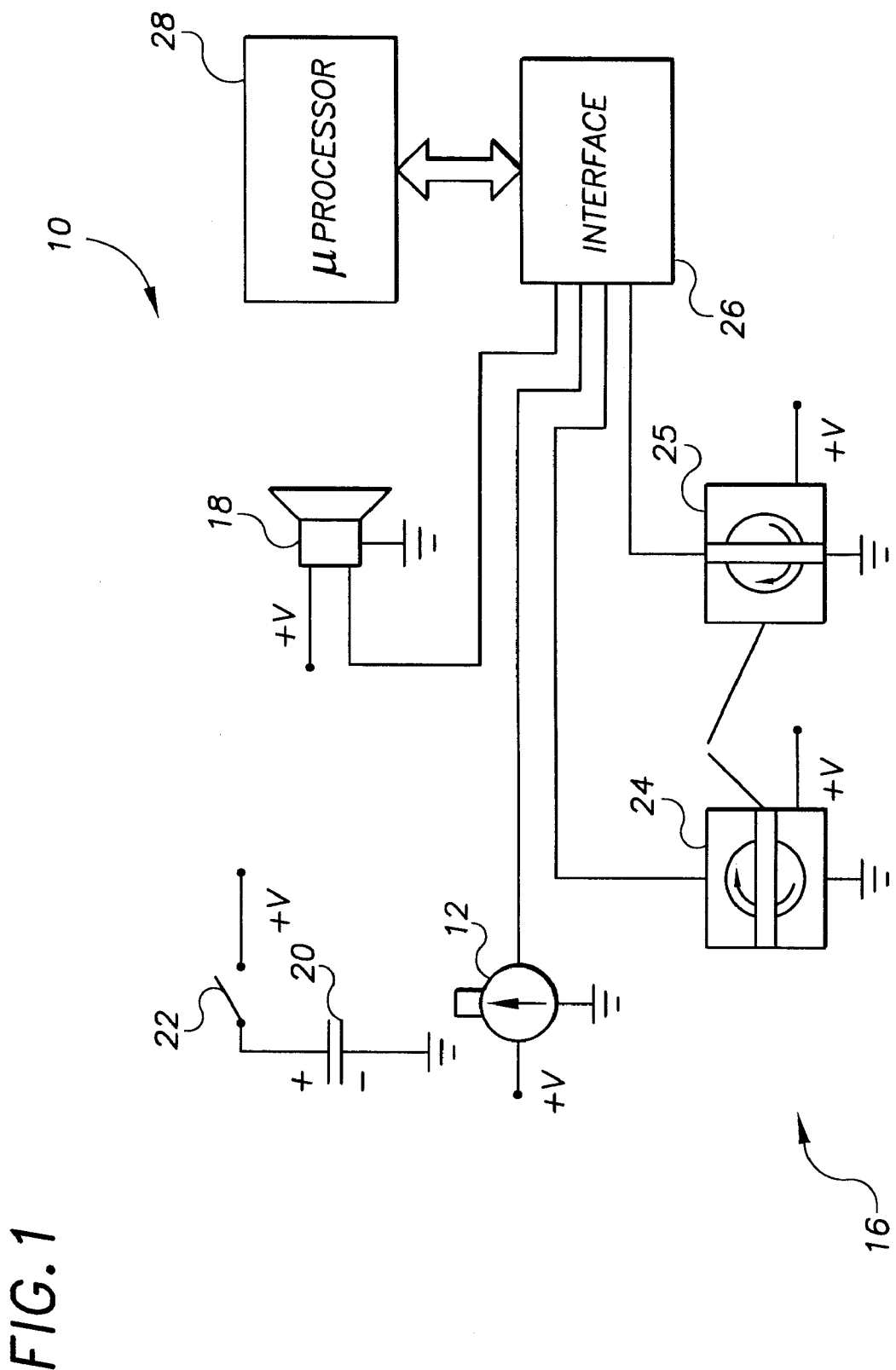
FIG. 1 is a schematic diagram of an exemplary embodiment of a hand-held CPR chest compression monitor.

FIG. 1 is a schematic representation of one embodiment of a hand-held CPR chest compression monitor 10 for measuring the rate and depth of chest compressions during the administration of CPR. The illustrated monitor 10 is a specific implementation of a monitoring system for measuring and prompting chest compressions to facilitate the effective administration of cardiopulmonary resuscitation (CPR). The system comprises a displacement detector and a signaling mechanism. The displacement detector produces and outputs a displacement-indicative signal indicative of the displacement of a CPR recipient's chest toward the recipient's spine. The signaling mechanism provides chest compression indication signals directing a chest compression force applied to the chest and a frequency of compressions to bring and maintain the frequency and chest displacement parameters within desired ranges. The monitoring system may be further provided with a tilt compensator comprising a tilt sensor mechanism outputting a tilt compensation signal indicative of the extent of tilt of the device. The system may further include an adjuster for adjusting the displacement value calculated from the measured acceleration signal in accordance with the output tilt compensation signal.

In the illustrated implementation, a hand-held CPR chest compression monitor 10 is provided. It comprises a displacement detector comprising an accelerometer 12 coupled to a microprocessor 28 via an interface 26. The illustrated interface 26 may comprise a parallel or serial interface which may be internal (where microprocessor 28 is provided as part of one integral device) or external (where microprocessor 28 is provided as a separate device). The signaling mechanism comprises an audible indicator (i.e., a loud speaker) 18, which has an input connected to microprocessor 28 via interface 26. A DC voltage power supply 20 is connected between a switch 22 and ground, and provides a DC voltage +V for powering the various components of the illustrated monitor 10, including the above-noted accelerometer 12 and audible indicator 18. Tilt compensation devices are provided which include a first gyro 24 and a second gyro 25. They each include outputs connected to microprocessor 28 via interface 26.

While the illustrated monitor uses an audible indicator, other types of indicators may be used in addition or as an alternative. For example, the indicator may comprise a vibrating mechanism, visual indicators (e.g., blinking LEDs), and so on.

The illustrated monitor 10 determines chest displacement from a double integration of an acceleration signal produced by accelerometer 12. Microprocessor 28 is provided to handle the calculations needed to perform the various functions of the illustrated monitor 10, including the double integration of the acceleration signal. The accelerometer 12 will preferably comprise a high-quality, inexpensive accelerometer, such as the Analog Devices ADXL05.

The ADXL05 accelerometer comprises a complete acceleration measurement System provided on a single monolithic IC. It comprises a polysilicon surface micro-machined sensor and signal conditioning circuitry which implement a force-balanced control loop. The accelerometer is capable of measuring both positive and negative acceleration to a maximum level of plus or minus 5 g. The sensor comprises 46 unit cells and a common beam. The unit cells make up a differential capacitor, which comprises independent fixed plates and central plates attached to the main beam that moves in response to an applied acceleration. These plates form two capacitors, connected in series. The sensor's fixed capacitor plates are driven differentially by two 1 MHz square waves: the two square wave amplitudes are equal but are 180 degrees out of phase from one another. When at rest, the values of the two capacitors are the same, and therefore, the voltage output at their electrical center (i.e., at the center plate) is 0. When there is an applied acceleration, the common central plate or "beam" moves closer to one of the fixed plates while moving farther from the other. This creates a miss-match in the two capacitances, resulting in an output signal at the central plate. The amplitude of the output signal varies directly with the amount of acceleration experienced by the sensor.

A self-test may be initiated with the ADXL05 accelerometer by applying a TTL "high" level voltage (>+2.0 Vdc) to the accelerometer self-test pin, which causes the chip to apply a deflection voltage to the beam which moves it an amount equal to −5 g (the negative full-scale output of the device).

In operation, accelerometer 12 of compression monitor 10 will move in various directions not limited to a simple vertical-only movement. In other words, monitor 10 will tilt on the CPR recipient's chest during the administration of CPR, which will cause the linear motion indicated by accelerometer 12 to be corrupted by non-linear tilt-induced movements. Accordingly, the above-described tilt sensor mechanism 16 is provided in the illustrated embodiment, to facilitate the determination of the true displacement of the chest in relation to the recipient's spine without errors caused by tilting of the device with respect to the chest. First gyro 24 produces an angular velocity signal indicating the measured angular velocity around a first horizontal longitudinal axis, and second gyro 25 outputs an angular velocity signal indicating the measured angular velocity around a second horizontal longitudinal axis positioned perpendicular to the first longitudinal axis. These angular velocity signals integrated to obtain angular displacement signals, which can be used to correct the measured linear displacement for tilt of the monitor 10.

First and second gyros 24 and 25 may comprise a Murata Gyrostar (piezoelectric gyroscope (ENC05E). This commercially available gyro is approximately 20×8×5 mm in size, and is designed for large-volume applications such as stabilizing camcorder images. This gyro uses the Coriolis principle, which means that a linear motion with a rotational framework will have some force that is perpendicular to that linear motion. The Coriolis force is detected and converted to a voltage output by piezoelectric transducer elements mounted on a prism bar. The voltage output is proportional to the detected angular velocity. In the illustrated embodiment, the two gyros are driven at slightly different frequencies in order to avoid interference.

Interface 26, in addition to a serial or parallel interface, may further comprise A/D and D/A converters, including a D/A converter for driving audio transducer 18 to indicate the amount of displacement and to prompt CPR at the correct rate (80-100 compressions per minute). The output from accelerometer 12 is routed through an A/D converter provided as part of interface 26 for digitization and subsequent analysis by microprocessor 28. Similarly, the output from each of first and second gyros 24 and 25 is routed to microprocessor 28 via an A/D converter provided as part of interface 26.

Microprocessor 28 is provided as part of a hand-held integrated module comprising monitor 10. As an alternative, a separate computer such as a lap top computer may be provided which is coupled to interface 26 (serving as an external interface) of the illustrated monitor 10.

Further information, regarding other types of inertial proprioceptive devices utilizing accelerometers and gyros, is provided by C. Verplaetse in an article entitled "Intertial Proprioceptive Devices: Self-Motion-Sensing-Toys and Tools," IBM Systems Journal, Vol. 35, Nos. 3 and 4 (1996) pages 639-650, the content of which is hereby expressly incorporated herein by reference in its entirety.

Figure 2:
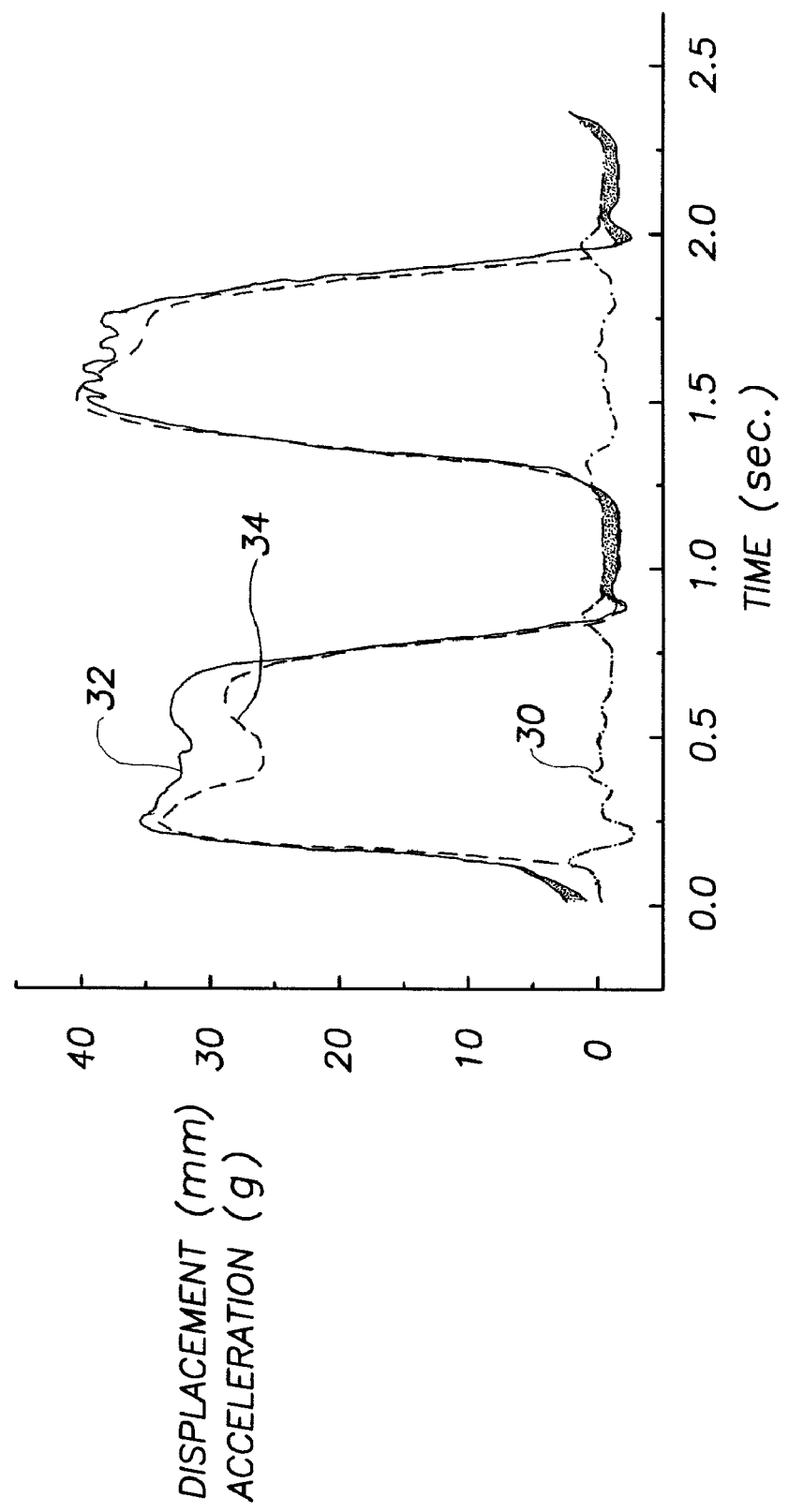
FIG. 2 is a waveform diagram comparing measured and calculated signals caused by manual compressions of a simulated chest of a CPR recipient.

FIG. 2 shows signals produced by a simulated recipient chest assembly. The simulated chest assembly was comprised of a spring connecting a block to a firmly supported base. Linear bearings where provided inside the block rode on a shaft to keep the block aligned vertically and to facilitate vertical movement of the block. A damper was coupled to the block to slow the movement of the block to simulate chest compliance. Vertical displacement of the block was measured by a position transducer (LVDT). A force transducer was attached to the top of the aluminum block, and provided signals indicative of the output forces as a result of CPR-like compressions. The assembly was calibrated and designed to closely mimic the visco-elastic properties of the human chest. The force transducer was calibrated with standard weights and the displacement transducer was calibrated with a ruler. An accelerometer (ANALOG DEVICES® ADXL-05) was mounted on a circuit board with appropriate biasing and filtering components, and the circuit board was attached to an aluminum holder. The accelerometer assembly was placed on a the simulated chest and manual compressions were applied.

FIG. 2 shows a comparison of actual displacement (measured by LVDT) and displacement calculated using the acceleration signals from the accelerometer assembly, during manual compressions of the simulated chest. The acceleration signals were doubly integrated and were plotted with the measured displacement and acceleration. The illustrated signals waveforms are displayed with respect to an abscissa representing a progression in time and an ordinate axis representing a value of either displacement in millimeters or acceleration g. The illustrated waveforms include an acceleration signal 30, a measured distance signal 32, and a calculated distance signal 34. FIG. 2 demonstrates the closeness of fit of the calculated and measured displacement, especially the maximum displacements, which is an important parameter.

Figure 3:
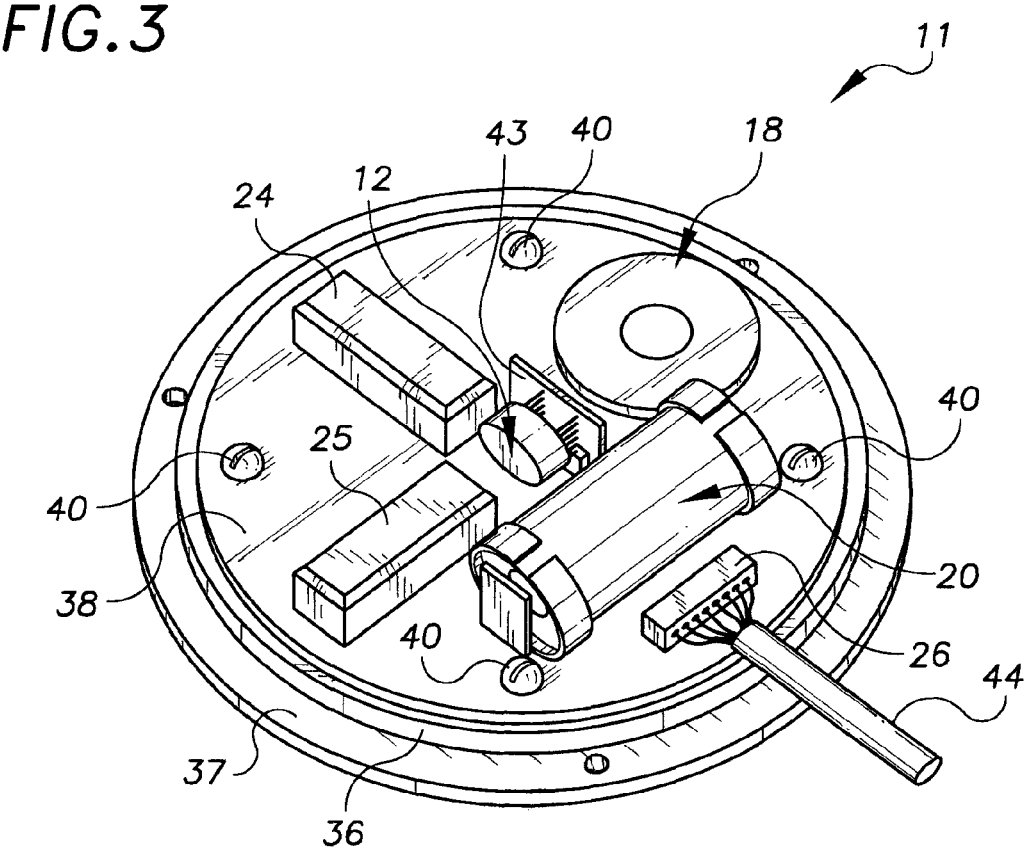
FIG. 3 is a perspective view of an exemplary mechanical layout of a hand-held module for monitoring CPR chest compressions.
Figure 4:
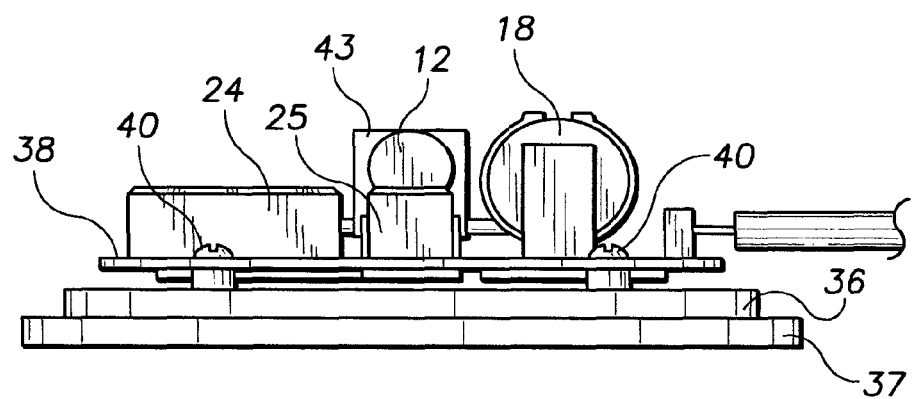
FIG. 4 is a side view of the module illustrated in FIG. 3.

FIGS. 3 and 4 show an exemplary mechanical layout of a hand-held module comprising a compression monitor 10, for example, implemented in accordance with the schematic diagram shown in FIG. 1. The illustrated module 11 comprises a circular base 36 having an outer flange portion 37. Mounted on base 36 is a circuit board 38. Circuit board 38 is fixed to base 36 by means of fasteners 40. A plurality of components are mounted directly on circuit board 38, including first and second gyros 24 and 25, accelerometer 12, indicator 18, power source 20, and interface 26.

The illustrated module is roughly 3 inches in diameter and 0.5 inches in height. FIG. 3 shows first and second gyros 24 and 25 mounted at right angles to each other on circuit board 38, which measure the angular velocity around each of their respective longitudinal axes. The illustrated accelerometer 12 is packaged in a TO-100 package (a 10 pin can), where the axis of sensitivity to acceleration (vertical) is perpendicular to the plane of circuit board 38. Accelerometer 12 is attached to a right angle support 43 which provides electrical connections with circuit board 38, as well as a rigid mounting surface.

Figure 5:
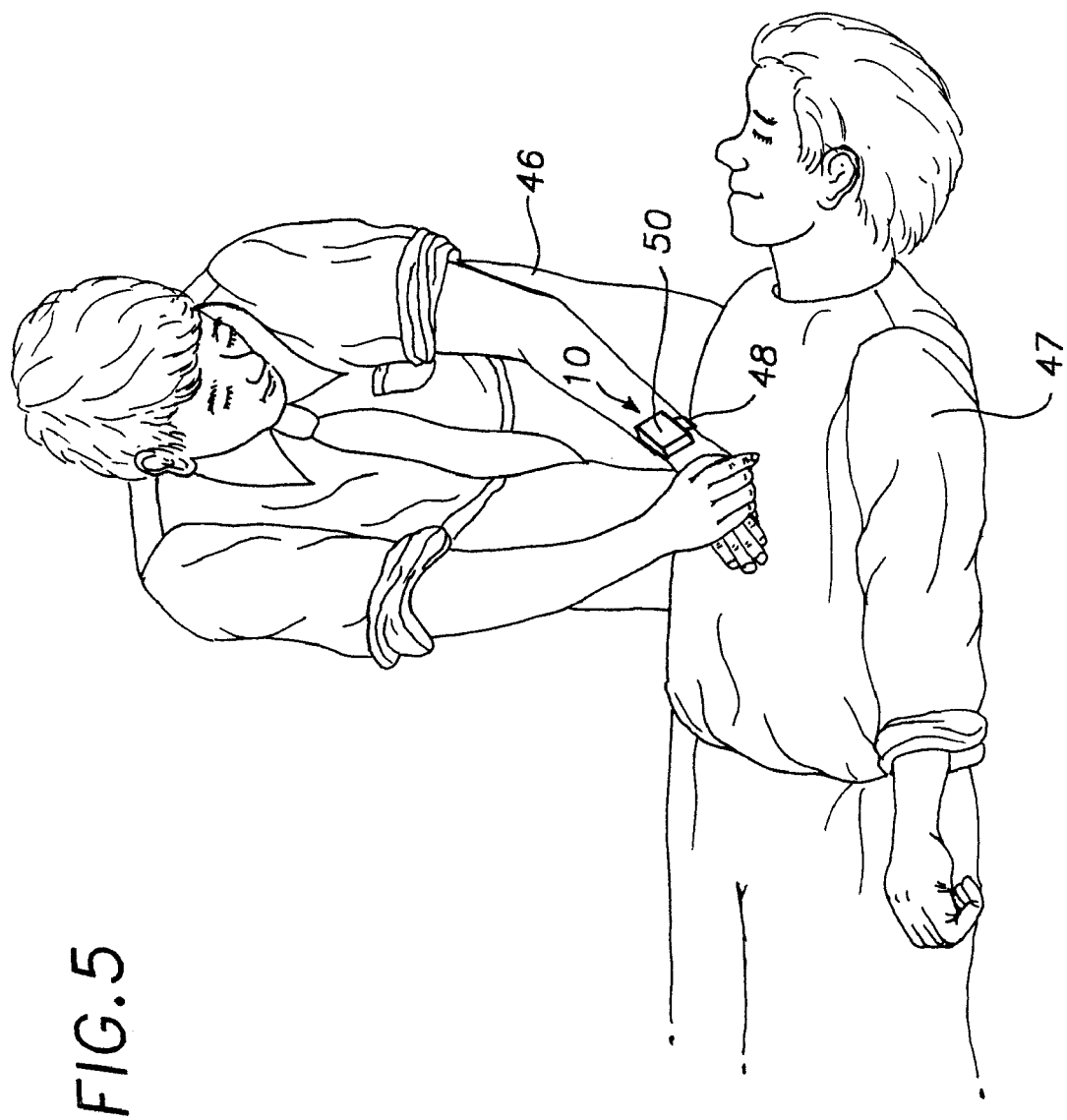
FIGS. 5-7 each show a rescuer administering CPR to a CPR recipient utilizing various embodiments of a CPR monitoring device according the present invention.
Figure 6:
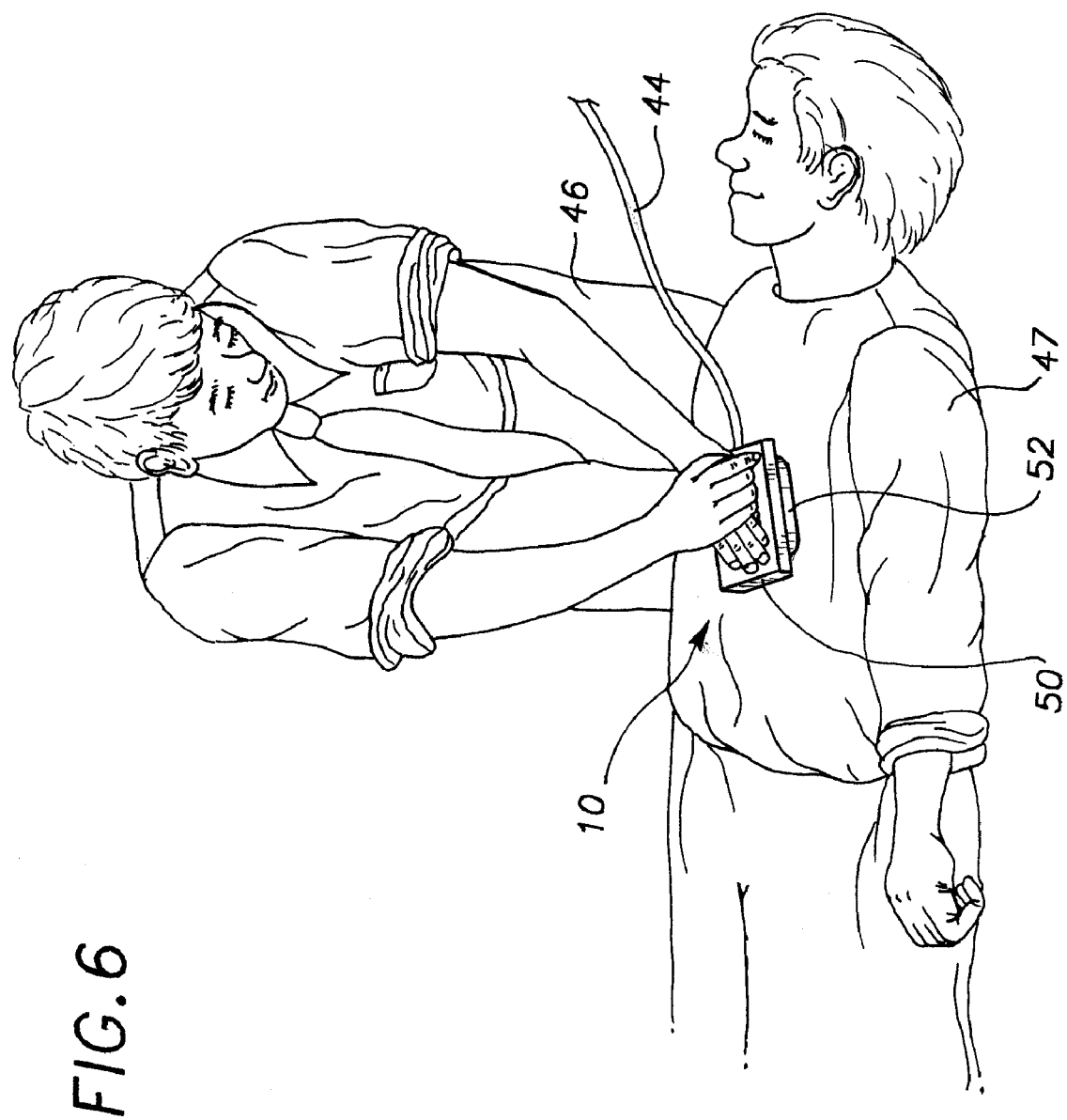
Figure 7:
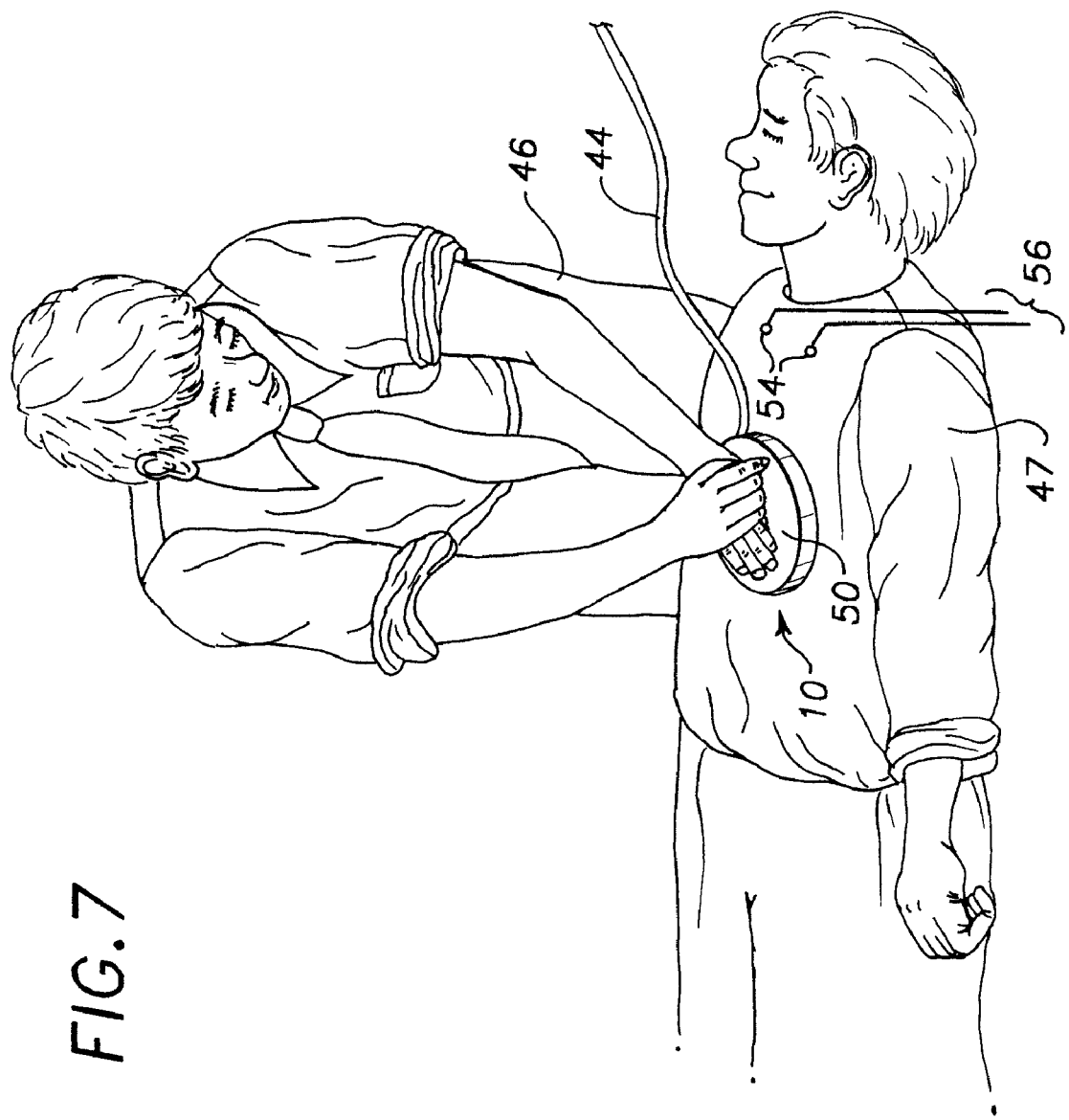

FIGS. 5-7 show various implementations of a hand-held device which may be utilized in connection with the illustrated compression monitor 10 disclosed herein.

FIG. 5 illustrates a rescuer 46 administering CPR to a recipient 47. The rescuer's hands are placed in contact with the recipient's chest at the proper location. A compression monitor 10 is attached to one of the rescuer's wrists at the point which is proximate to the point at which rescuer 46 is exerting force on the recipient's chest during CPR. The illustrated monitor 10 comprises a mount coupled a housing portion of the monitor. In the illustrated embodiment, the mount comprises a releasable fixing mechanism, i.e., a band 48 for releasably fixing housing portion 50 (containing the various components of monitor 10, such as those shown in FIG. 1) to the rescuer's 46 extremity (wrist).

In FIG. 6, a compression monitor 10 comprises a housing 50, and a compression force translating piece 52 positioned thereunder for focusing the force exerted by rescuer 46 to a desired area downwardly against the chest of the CPR recipient, in the direction facing the recipient's spine. The hand-held monitor 10 illustrated in FIG. 6 may comprise a cable 44 for coupling monitored signals to a computing device (not shown) which is separate from the handheld device. In the alternative, a processor may be integrally provided within housing 50, in which case cable 44 would not be necessary.

In FIG. 7, hand-held monitor 10 comprises a unitary disc-like housing 50, upon which rescuer 46 places his or her hands. Each of the versions of the compression monitor 10 shown in FIGS. 6 and 7 thus provides on top of housing 50 a receiving portion for directly receiving a downwardly acting force from the hands of rescuer 46 proximate to a point at which rescuer 46 is exerting force on the recipient's chest during CPR. Depending upon whether housing 50 already contains a microprocessor, an external cable 44 may be provided for coupling the electrical components within housing 50 to, for example, an external signal monitoring system or a computer. ECG electrodes 54 are coupled to respective ECG signal lines 56 and an ECG monitor device (not shown).

A mechanism (e.g., a self-contained ECG display) may be provided within the illustrated compression monitor 10 for displaying and/or processing the ECG signals; accordingly, alternatively, ECG signal lines 56 may be coupled to compression monitor 10.

In operation, the illustrated compression monitor 10 of either of the embodiments shown in FIGS. 5-7 will facilitate the effective administration of CPR by producing a displacement-indicative signal indicative of the displacement of the recipient's chest toward the recipient's spine. Specifically, the audible indicator provided within device 10 is modulated to indicate when the proper chest displacement is achieved. That is, when a chest displacement in a desired range is achieved by rescuer 46, the audible indicator will output a modulated signal having a first pitch, while if the displacement is out of range, the frequency of the modulated signal will be at a second pitch. The amplitude of the audible indication may be pulsed to coincide with the desired frequency of chest compressions. Alternatively, the audible indicator can provide, together, with appropriate signal processing components, verbal indications to the rescuer 46, i.e., serving as voice prompts to the rescuer. As another alternative, an audio transducer may be provided which outputs a beeping sound to prompt the user to compress at the proper rate.

Figure 8:
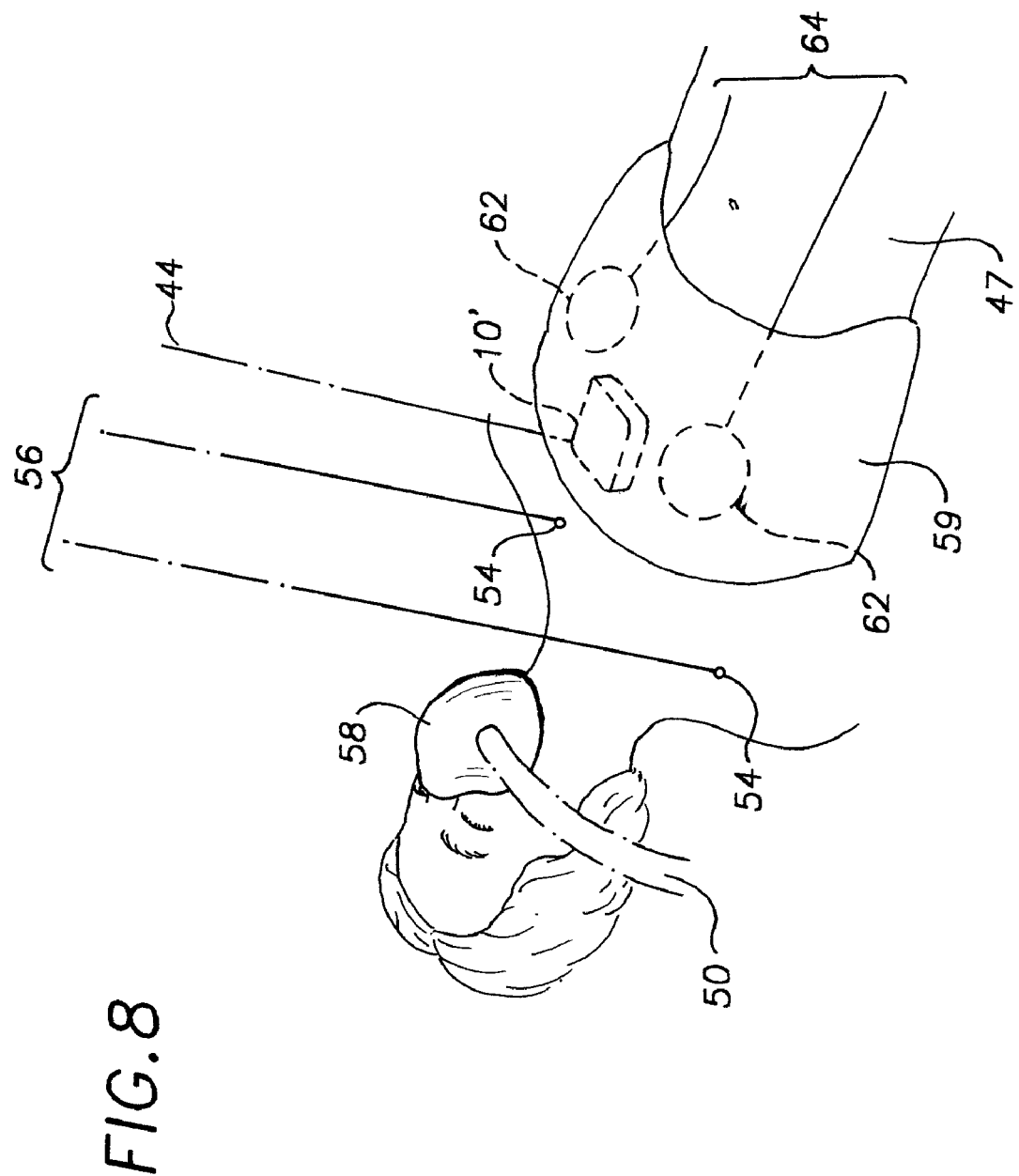
FIG. 8 shows a CPR recipient coupled to various resuscitation assistance apparatuses.

FIG. 8 shows a CPR recipient connected to various resuscitation-aiding apparatuses, including an automated constricting device 59 for automatically administering CPR to the recipient. Automated constricting device 59, more specifically, applies inwardly radial forces against the recipient's chest in order to cause a desired chest displacement in the direction toward the recipient spine at a desired chest compression frequency.

Additional apparatuses connected to the recipient include a ventilator mask 58 coupled to an air tube 60, ECG electrodes and corresponding ECG signal lines 56, defibrillation electrodes 62, and a CPR chest compression monitor 10' coupled to a cable 44, for carrying signals generated thereby, including a detected acceleration signal.

The overall assembly facilitates the resuscitation of a recipient 47 in an automated fashion. Such a set up can be particularly useful in various situations, for example, including the case where the recipient is being carried in an ambulance vehicle. Resuscitation efforts could be continued while the recipient is being transported, thus increasing the chance of survival by providing resuscitation efforts as soon as possible while transporting the recipient to the hospital.

As illustrated, the recipient is hooked up to a ventilation apparatus comprising a ventilator mask 58, which will allow respiration efforts to be administered. The patient's ECG and associated heart rhythm information can be monitored by ECG signal lines 56 coupled to an ECG monitor device (not shown). CPR can be automatically administered by automated constricting device 59. Timely defibrillation can be administered with the use of defibrillation electrodes 62 coupled via defibrillation lines 64 to a defibrillation device (not shown). The automated constricting device 59 can be controlled by signals produced by compression monitor 10' so that the proper compression forces are applied to the recipient's chest at the appropriate frequency.

In addition, the acceleration signal produced by compression monitor 10' can be retrieved via cable 44 and used to process the ECG signal obtained via ECG signal lines 56 concurrently with the administration of CPR. More specifically, when CPR is administered, the ECG signal may be affected and thus include a CPR-induced artifact. An ECG processor, which will be further described below, may be provided to process the ECG signal so as to remove the CPR-induced artifact and render the resulting processed ECG signal meaningful and intelligible.

The automated constricting device 59 may comprise, for example, the CPR vest apparatus disclosed in the commonly-assigned co-pending patent application filed concurrently and on even date herewith in the name of Dr. Henry Halperin, or it may comprise an automated CPR system as disclosed in U.S. Pat. No. 4,928,674 (Halperin et al). The content of each of these references is hereby expressly incorporated herein by reference in its entirety.

In the assembly shown in FIG. 8, an automated constriction controller (not shown) is provided together with the automated constricting device for applying CPR to the recipient 47 by applying a constricting force to the chest of the recipient 47 under control of the automated controller. The automated controller receives the chest compression indication signals from compression monitor 10', and, in accordance with the chest compression indication signals, controls the force and frequency of constrictions applied to the CPR recipient's chest.

Figure 9:
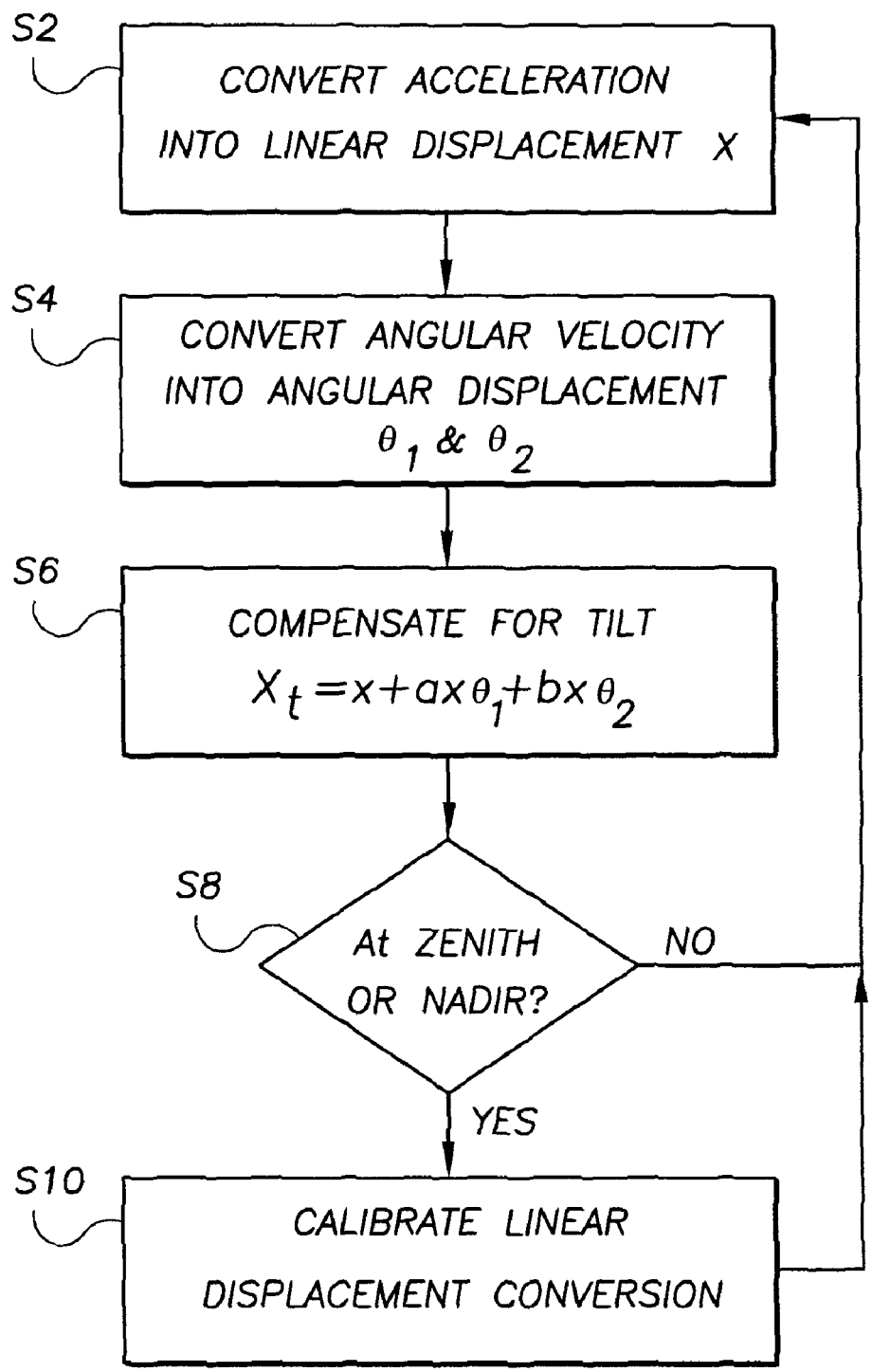
FIG. 9 is a flow chart of the process utilized by the chest compression monitor illustrated in FIG. 1 in order to convert a detected acceleration signal into a displacement value.

FIG. 9 is a flow chart illustrating a process for converting the acceleration and tilt signals produced by the compression monitor 10 shown in FIG. I into a displacement-indicative signal, and for calibrating the conversions. The illustrated process may be performed by, for example, microprocessor 28 as shown in the embodiment illustrated in FIG. 1.

In a first step S2, the acceleration signal is converted into a linear displacement x. Then, in step S4, the angular velocity signals output by each of first and second gyros 24 and 25 are converted into respective angular displacements theta 1 and theta2. In step S6, the displacement x is compensated for the tilting, thus producing a tilt-compensated linear displacement value xt which is equal to x+ax(theta1)+bx(theta2).

During each chest compression cycle (usually 600-700 ms), the device will come to rest twice: at the zenith and nadir of the compression. These two time points may be easily identified since the vertical acceleration at these times will be 0, and there will be a change in the direction of the velocity, Accordingly, at step S8, a determination is made as to whether the device is at the zenith or nadir. If it is, the linear displacement conversion is calibrated at step S 10. If not, the process will return to step S2. In calibrating the linear displacement conversion, at step S 10, measurements are made at the rest point to re-calibrate the system and eliminate the components $v_0$, $\chi_0$ from the equation (noted below) utilized to convert acceleration in to linear displacement x.

Algorithms are well known for converting an acceleration signal (from an accelerometer) into linear displacement and for converting an angular velocity signal (from gyros) into an angular displacement. In general, inertial navigation systems may determine position and orientation from the basic kinematic equations for transitional and rotational motion. The orientation of an object, given a sensed rotational rate, w, during each time step t, is given by:

$$\theta = \theta_0 + wt \quad (1)$$

where $\theta$ equals the orientation angle, t equals the time step and w is the rotational rate output by a gyroscope.

Similarly, position is found with the transitional kinematic equation:

$$x = \chi_0 + v_0 t + (0.5)at^2, \quad (2)$$

where x equals position, v equals velocity and a equals acceleration, output by an accelerometer.

Motion and position may be estimated with equations, (1) and (2). Alternatively, motion and position may be estimated using a Kalman filter state estimation algorithm. Once the time-dependent motions and positions of the system are estimated, a pattern recognition scheme such as a neural network, hidden Markov model, or matched filter may be performed with that motion data. The true vertical displacement $\chi^r$ may be estimated as a combination of one translation and two angular displacement x, theta$_1$, and theta$_2$. It is expected that within the expected angular deviation range of +/−30 degrees from vertical a simple equation (3) will work:

$$\chi_a = x + ax(\text{theta}_1) + bx(\text{theta}_2) \quad (3)$$

Coefficients a and b may be determined empirically using best linear fit methods, or a more complex non-linear model, as appropriate.

In the event thermal drift is a factor, additional circuitry may be provided as part of the compression monitor for thermal compensation.

While resuscitation is in progress, it is vital that health care personnel can be continuously aware of changes in the patient's ECG, in particular the patient's heart rhythm. Incorrect assessment of the heart rhythm can lead to improper therapy. However, when CPR is administered, CPR-introduced artifacts will be present in the measured ECG signal that make interpretations difficult. FIGS. 10-16 provide various system models, analysis waveform diagrams, and proposed ECG processing embodiments for addressing this problem.

Figure 10:
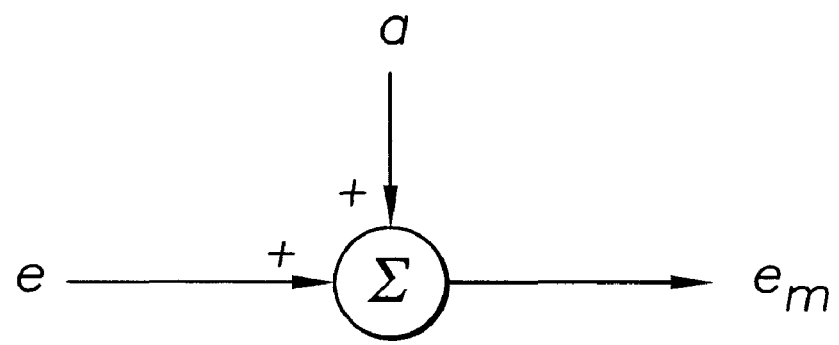
FIG. 10 is a schematic diagram illustrating a model of a system comprising a CPR recipient receiving CPR while an ECG monitor connected to the CPR recipient generates a measured ECG signal $e_m$.

As shown in FIG. 10, it can be assumed that the measured ECG signal $e_m$, for example, obtained on ECG signal lines 56, is equal to the sum of the true ECG signal e and the true CPR noise signal a (the CPR-induced artifact). A goal of the present invention is to provide a subsystem, into which the measured ECG signal $e_m$ is input, and from which a processed measured ECG signal $e_m'$, absence the CPR-induced artifact, is output.

Figure 11:
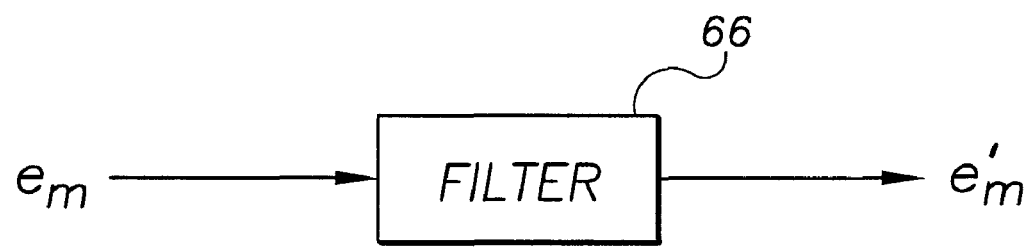
FIG. 11 provides a model for the conversion of a measured ECG signal $e_m$ to a processed measured ECG signal $e_m'$.

As an initial approach toward eliminating the CPR induced artifact, a band pass filter 66 as shown in FIG. 11 may be utilized. In this approach, the measured ECG $e_m$ is viewed as the superposition of a true ECG e and CPR noise. Filter 66 selectively preserves as much of the ECG signal as possible, while suppressing the artifact as well as possible. The problem with this approach is that it is difficult to separate the true ECG from the CPR-induced artifact since components of each of those signals coexist in the same portions of the frequency domain.

Figure 12:
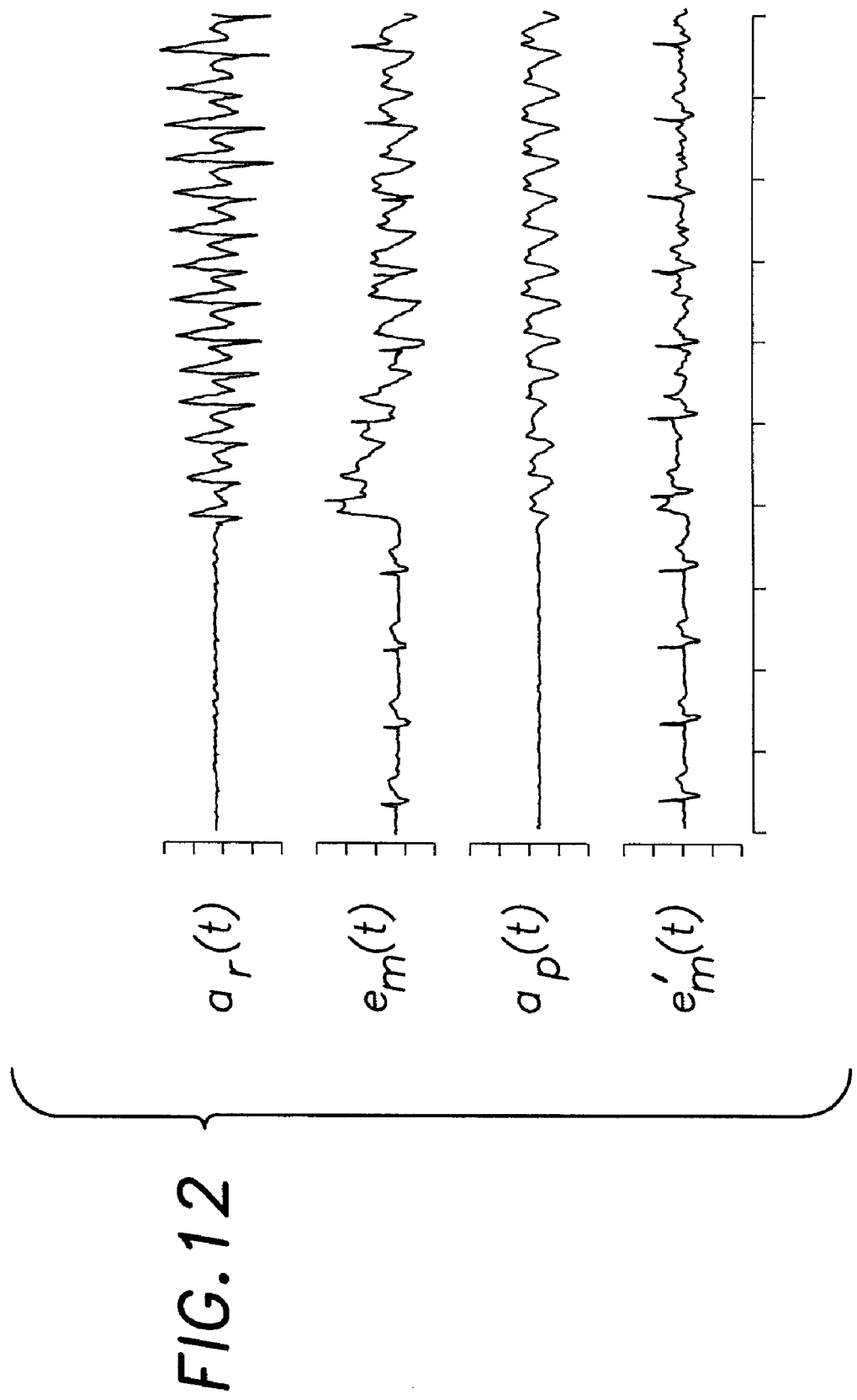
FIG. 12 is a waveform diagram showing the respective waveforms $a_r$, $e_m$, $a_p$, $e_m'$.

FIG. 12 shows several waveforms pertinent to the processing of a CPR-affected ECG signal. A first waveform $a_r$ represents a measurable signal which "represents" the CPR-induced artifact. That signal may comprise a force, acceleration, distance, velocity, motion, or vest signal, each of which represents some aspect of the CPR-induced artifact. In the illustrated embodiment, the signal $a_r$ comprises the acceleration signal produced by the accelerometer 12 of the device shown in FIG. 1.

The next waveform is the measure ECG signal $e_m$, measured during CPR. The following waveform $a_p$ is the predicted artifact. The last waveform $e_m'$, is the processed measured ECG signal, which has been processed to remove the CPR-induced artifact. The processed measured ECG signal $e_m'$ shown in FIG. 12 was produced using linear predictive filtering as will be described below.

Figure 13:
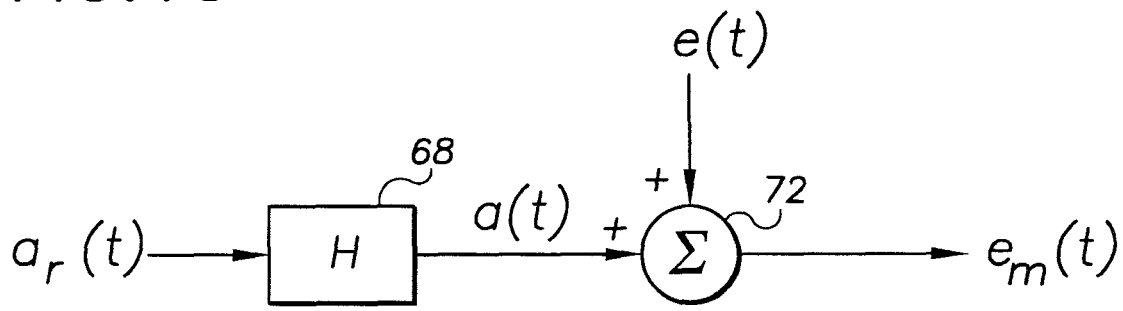
FIG. 13 shows another model of a system involving the administration of CPR to a patient, monitoring of chest compressions, producing a measured acceleration signal, and producing a measured ECG signal.

When a true ECG e and artifactual components a overlap in both time and frequency domains, it is still possible to distinguish the two if a separate signal that is correlated with the artifact is available. The system that gives rise to the measured ECG signal $e_m$ can be modeled as the sum of the true ECG e and an artifact waveform a. This model is shown in FIG. 13. The true CPR noise signal a is treated as the output of a linear system $\tilde{H}$ perturbed by a measurable input $a_r$.

The goal of linear predictive filtering, in accordance with the embodiment disclosed herein, is to identify the linear system $\tilde{H}$ that transforms the acceleration signal $a_r$ into the waveform composed of the artifactual components, i.e., a, in the measured ECG $e_m$. Once this system is identified, the artifactual component can be predicted, using linear predictive filtering, by taking the output $a_p$ of a simulated system $\tilde{H}$, using the acceleration signal $a_r$ as the input. When this linearly predicted signal $a_p$ is subtracted from the measured ECG $e_m$, the resulting signal is the estimated true ECG, which is shown as the processed ECG signal $e_m'$ in the output of the system shown in FIG. 14.

Figure 14:
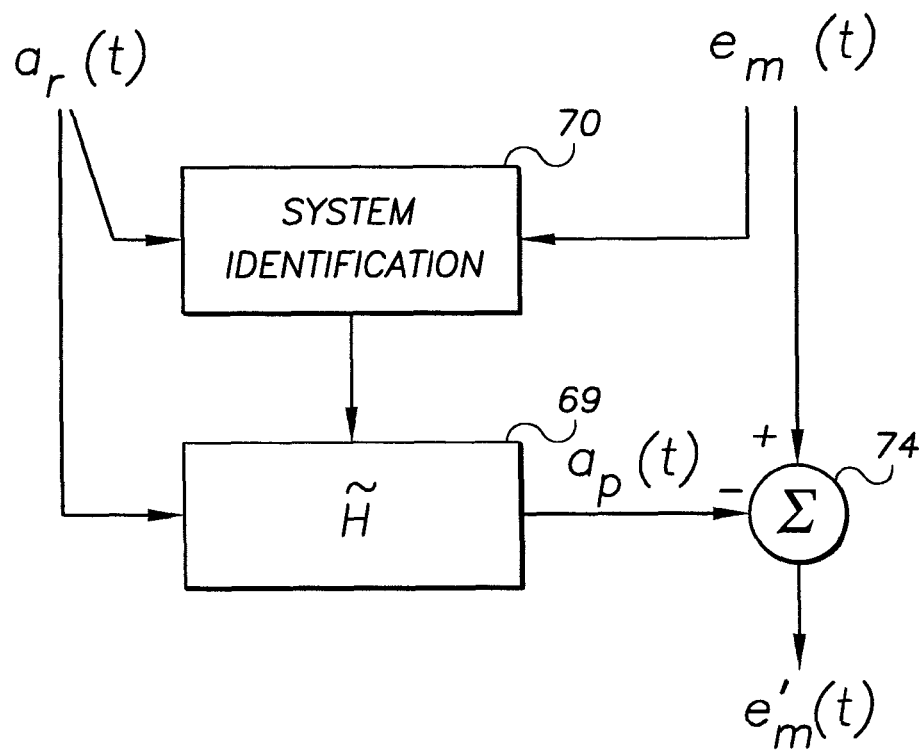
FIG. 14 illustrates a mechanism provided in accordance with a specific aspect of the invention for identifying a system and using the identified system to produce a processed measured ECG signal which is processed to remove a CPR-induced artifact.
Figure 15:
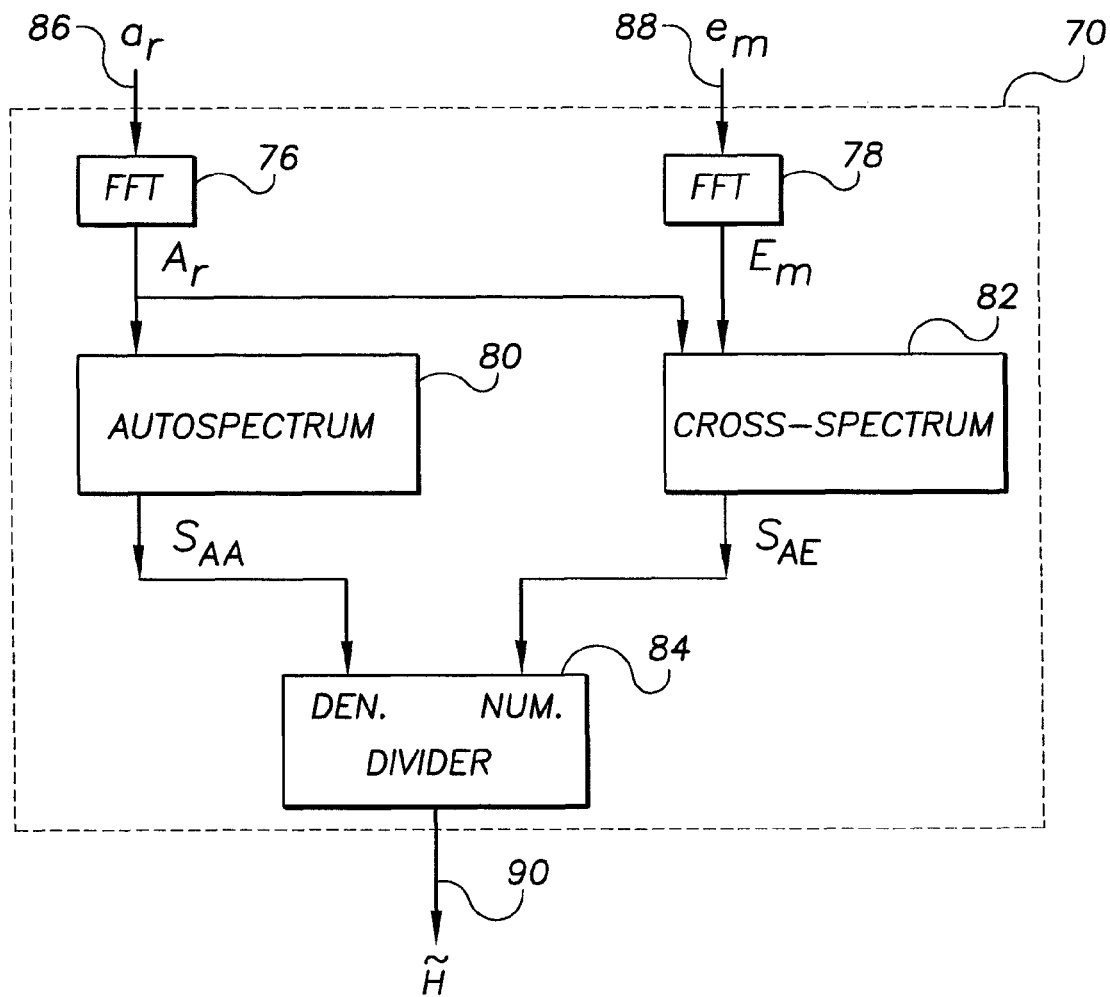
FIG. 15 shows a block diagram representation of a first embodiment ECG signal processor.

FIG. 15 shows a specific exemplary embodiment of the system identification process 70 shown in the embodiment of FIG. 14. The system identification block 70 comprises a correlated signal input $a_r$ 86 and a non-correlated signal input $e_m$ 88. Correlated signal input 86 is input to a first FFT 76, while non-correlated signal input 88 is input through a second FFT 78. The output of first FFT 76 is input to a autospectrum calculator 80 and to cross-spectrum calculator 82. The output of second FFT 78 is input to cross-spectrum calculator 82.

The output of the first FFT 76 is the frequency domain representation of the measured signal $a_r$ and the output of the second FFT 78 is the frequency domain representation of the measured ECG signal $e_m$. Autospectrum calculator 80 outputs Saa which is the input signal's autospectrum, while cross-spectrum 82 outputs Sae which is the cross-spectrum between the observed input and output signals. These can be computed using Fourier transform techniques, for example, as disclosed by Jenkins et al. "Spectral Analysis and its Applications," Holden Day, Oakland, Calif. (1968), and R. D. Berger, "Analysis of the Cardiovascular Control System Using Broad-Band Stimulation," Ph.D. Thesis, MIT (1987), the content of each of which is hereby expressly incorporated herein by reference in its entirety.

The input signals autospectrum Saa is then input into the denominator input of a complex divider 84, while the cross-spectrum Sae (between the observed input and output signals) is input to the numerator input of divider 84. Divider 84 performs complex division on its input signals in order to produce at its output 90 a complex representation of the estimated transfer function $\tilde{H}$. The transfer function $\tilde{H}$ can be updated periodically from new short segments of input signals, which may include the acceleration signal output by the accelerometer and the measured ECG signal. The processed ECG signal $e_m'$ output by the system shown in FIG. 14 is produced utilizing the overlap and add technique.

Instead of system $\tilde{H}$ being a linear system, a non-linear system may be estimated instead and used to subtract the CPR-induced artifact from the measured ECG signal.

Figure 16:
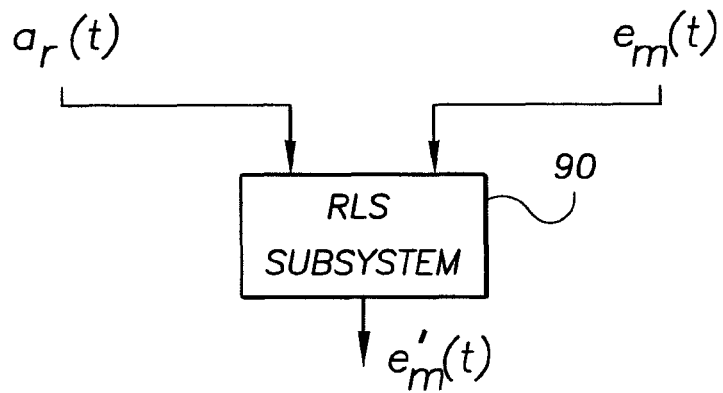
FIG. 16 shows a block diagram representation of a second embodiment ECG signal processor.

As an alternative to the systems shown in FIGS. 14 and 15, a recursive least squares (RLS) subsystem 90 may be provided as shown in FIG. 16.

In accordance with the recursive least squares method, each time a new data sample is input to each of the inputs of the subsystem, the recursive model is modified on an ongoing basis. Techniques for utilizing the recursive least squares method to produce an RLS subsystem 90 as shown in FIG. 16 are known in the art. For example, reference may be made to L. Ljung et al., "Theory and Practice of Recursive Identification," the MIT Press, Cambridge, Mass. (1986), the content of which is hereby expressly incorporated by reference herein in its entirety.

The following is an example program listing which may form the basis for employing an RLS subsystem.

---

```
x: input (acceleration), y: measured output, z: predicted output
linpred ( x, y, z, npts, in, n)
float *x, * Y, *z;
long npts;
int m, n;   /* m: MA order, n: AR order */
{
```

```
double phi [MAXARMALEN], theta [ MAXARMALEN], 1
[MAXAPMALEN];
double p [MAXARMALEN] [MAXARMALEN], alpha=1.0
double array 1 [MAXARMALEN], array2 [MAXARMALEN], c;
double mat[MAXARMALEN][MAXARMALEN],
mat2[MAXARMALEN] [MAXARMALEN],
int i, j, k;
    for (k = 0; k<m+n; k++) {
        theta[k] = 0;
        for(j=O; j<m+n; j++) {
            if( j --k )
                p[k] [j] -LARGE;
            else
                p[k] [j] 0;
        }
    }
    for (i-0; 1<m+n, i++)
        z [i] = y[i];
    for ( i = m+n; i<npts; i++) {
        j=0;
        for( k= 1; k<=n; k++) {
            phi [j] = -y[i-k];
            j++;
        }
        for( k= 1; k<=m; k++) {
            phi[j] = x[i-k];
            j++;
        }
        mat_array_mult ( p, phi, array 1, m+n);
        arrayt_array_mult ( phi, array 1, &c, m+n);
        array_k_mult ( array 1, 1/alpha + c, 1, m+n);
        arrayt_mat_mult ( phi, p, array2, m+n );
        array_arrayt_mult (1, array2, mat1, m+n);
        mat_mat_subtract (p, mat1, mat2, m+n)
        mat_copy (mat2, p, m+n);
        arrayt_array_mult ( theta, phi, &c, m+n);
        array_k_mult ( 1, y[i]-c, array 1, m+n );
        array_array_add ( theta, array1, array2, m+n);
        array_copy ( array2, theta, m+n );
        arrayt_array_mult ( theta, phi, &c, m+n);
        z[i] = c;
        printf ("%2f/n", c );
    }
}
mat_array_mult (a, b, c, dim)
double a [ ] [MAXARMALEN], *b, *c;
int dim;
{
int i, j;
    for (i = 0; i<dim; i++) {
        c[i] = 0
        for (j-0; j<dim; j++)
            c[i] + = a[i][j]j *b[j];
    }
}
array_array_mult (a, b, c, dim)
double *a, *b, *c;
int dim;
[
int i;
    *c = 0;
    for ( i=O; i<dim; i++)
        *c + a[i] *b[i];
}
array_mat_mult (a, b, c, dim)
double *a, b[ ] [MAXARMALEN], *c;
int dim;
{
int i,j;
    for i=O; i<dim; i++) {
        c[i] - 0;
        for( j=O; j<dim;j++)
            c[i] + = a[i] *b[j][i]
    }
}
array_arrayt_mult ( a, b, c, dim)
double *a, *b, c[ ] [MAXARMALEN];
int dim;
{
int i,j;;
    for ( i=O; i<dim; i++)
        for ( j=O; j<dim; j++)
            c[i][j] − a[i]*b[j];
}
array_k_mult ( a, b, c, dim)
double *a, b, *c;
int dim;
{
int i;
    for i=0 i<dim; i++)
        c[i] = a[i]*b;
}
mat_mat_subtract ( a, b, c, dim)
double a[ ][MAXARMALEN], b[ ] [MAXARMALEN], c[ ] [MAXARMALEN];
int dim;
{
int i,j;
    for ( i=O; i<dim; i++)
        for j=0; j<dim; j++)
            c[i][j] = a[i][j] − b[i][j];
}
array_array_add( a, b, c, dim)
double *a, *b, *c;
int dim;
{
int i;
    for ( i=O; i<dim; i++)
        c[i] = a[i]+b[i];
}
mat_copy (a, b, dim)
double a[ ][MAXARMALEN], b[ ][MAXARMALEN];
int dim;
{
int i, j;
    for (i=O; i<dim; i++)
        for (j=0; j<dim; j+1)
            b[i][j] = a[i][j];
}
array_copy ( a, b, dim)
double *a, *b;
int dim;
{
int i;
    for ( i=O; i<dim; i++)
        b[i] = a[i];
}
```

While the invention has been described by way of example embodiments, it is understood that the words which have been used herein are words of description, rather than words of limitation. Changes may be made, within the purview of the appended claims, without departing from the scope and spirit of the invention in its broader aspects. Although the invention has been described herein with reference to particular structures, materials, and embodiments, it is understood that the invention is not limited to the particulars disclosed. Rather, the invention extends to all appropriate equivalent structures, mechanisms, and uses.

We claim:

1. A system for monitoring the compression of the chest of a patient, said system comprising:
a chest compression monitor adapted to follow the movement of the chest of a patient undergoing compression, said chest compression monitor comprising an accelerometer adapted to sense upward and downward acceleration of the chest compression monitor, said compression monitor further adapted to output an acceleration signal indicative of the upward and downward acceleration of the chest, said compression monitor housed in a module adapted to be held in fixed relationship to the top of the chest during chest compression without connection to a reference external to the compression module;

a computer programmed to process the acceleration signal to determine the depth of chest compression and produce a compression signal indicative of the depth of compression of the patient's chest, said computer further programmed to determining the start of a compression without reference to a signal derived from a source external to the module, and thereafter calculate downward displacement of the chest using the acceleration signal; said computer further programmed to output a compression signal.

2. The system of claim 1 wherein:
the computer is further programmed to determine the end of a compression, and thereafter calculate upward displacement of the chest using the acceleration signal.

3. The system of claim 1 wherein:
the computer is further programmed to determine the start of a compression based on the acceleration signal, a zero-point of acceleration and changes in the direction of velocity of the module.

4. The system of claim 1 wherein:
the computer is further programmed to determine the end of a compression based on the acceleration signal, a zero-point of acceleration and changes in the direction of velocity of the module.

5. A method for monitoring the compression of the chest of a patient, said method comprising:
providing a chest compression monitor adapted to follow the movement of the chest of a patient undergoing compression, said chest compression monitor comprising an accelerometer adapted to sense upward and downward acceleration of the chest compression monitor, said compression monitor further adapted to output an acceleration signal indicative of the upward and downward acceleration of the chest, said compression monitor housed in a module adapted to be held in fixed relationship to the top of the chest during chest compression; and
a computer adapted to process the acceleration signal to determine the depth of chest compression and produce a compression signal indicative of the depth of compression of the patient's chest;
placing the accelerometer in fixed relationship with the chest so that it follows the movement of the chest, without connecting the accelerometer to a reference external to the compression module;
causing at least one compression of chest of the patient;
processing the acceleration signal with the computer, and determining the start of a compression, and thereafter calculating downward displacement of the chest using the acceleration signal; and
producing the compression signal.

6. The method of claim 5 further comprising the step of:
determining the end of compression, and thereafter calculating upward displacement of the chest using the acceleration signal.

7. The method of claim 5 further comprising:
determining the start of a compression based on the acceleration signal, a zero-point of acceleration and changes in the direction of velocity calculated by the computer.

8. The method of claim 6 further comprising:
determining the end of a compression based on the acceleration signal, a zero-point of acceleration and changes in the direction of velocity calculated by the computer.

9. The method of claim 5 further comprising:
repeatedly compressing the chest, causing a plurality of chest compressions, and determining the start of each compression based on the acceleration signal, a zero-point of acceleration and changes in the direction of velocity calculated by the computer.

10. The method of claim 6 further comprising:
repeatedly compressing the chest, causing a plurality of chest compressions, and determining the end of a each compression based on the acceleration signal, a zero-point of acceleration and changes in the direction of velocity calculated by the computer.

11. A method for determining a displacement of a chest of a patient, the method comprising the steps of:
providing a compression monitor comprising an accelerometer capable of measuring the acceleration of a CPR recipient's chest during CPR;
placing the compression monitor on the CPR recipient's chest without connecting the compression monitor to an external reference, and thereafter performing CPR by performing compressions on the patient's chest;
measuring the acceleration with the accelerometer without reference to a reference external to the compression monitor; and
determining the zero points of acceleration; and
calculating the displacement of the chest of the patient using the measured acceleration and the zero points of acceleration.

12. A system for facilitating the administration of cardiopulmonary resuscitation (CPR), said system comprising:
an accelerometer for producing an acceleration signal indicative of the displacement of a CPR recipient's chest, said accelerometer housed in a module adapted to be held in fixed relationship to the chest during chest compression;
a microprocessor being programmed to convert the acceleration signal into a distance value indicative of the displacement of the CPR recipient's chest caused by CPR and compare the distance value to a desired range; and
said microprocessor being further programmed to output a signal corresponding to the distance value indicative of the displacement of the CPR recipient's chest;
wherein the distance value is determined from the acceleration signal, without reference to a signal derived from a source external to the module.

13. A method for facilitating the administration of cardiopulmonary resuscitation (CPR) using a compression monitor, said method comprising:
providing an accelerometer and a means for disposing the accelerometer in fixed relation to a CPR recipient's chest, said accelerometer housed in a module adapted to be held in fixed relationship to the chest during chest compression;
measuring, using the accelerometer, an acceleration signal of the compression monitor during chest compressions;
converting, using a microprocessor electrically connected to the accelerometer, the acceleration signal into a linear displacement signal indicative of the displacement of a CPR recipient's chest caused by CPR, wherein the linear displacement signal is determined without reference to a signal derived from a source external to the module; and
providing a signal corresponding to the distance value indicative of the displacement of the CPR recipient's chest.

14. The method according to claim 12, further comprising the steps of:
signaling, using a signaling mechanism operably connected to the processor, when the linear displacement signal is within a predetermined range.

15. The method according to claim 13, further comprising the steps of:
- signaling, using a signaling mechanism operably connected to the processor, when the linear displacement signal is within a predetermined range.

16. The method according to claim 12, further comprising the steps of:
- providing an automated constricting device and controlling said automated constricting device based on the signal corresponding to the distance value indicative of the displacement of the CPR recipient's chest.

17. The method according to claim 13, further comprising the steps of:
- providing an automated constricting device and controlling said automated constricting device based on the signal corresponding to the distance value indicative of the displacement of the CPR recipient's chest.

18. A method for facilitating the administration of cardiopulmonary resuscitation (CPR) on a patient by using a compression monitor to detect the depth of chest compressions while performing chest compressions and while the patient and the compression monitor are also subject to accelerations caused by forces other than those created by the administration of CPR, said method comprising the steps of:
- providing a compression monitor comprising an accelerometer, said accelerometer housed in a module adapted to be held in fixed relationship to the chest during chest compression, and a microprocessor operably connected to the accelerometer, said microprocessor programmed to convert the acceleration signal into a distance value indicative of the displacement of the CPR recipient's chest caused by CPR and programmed to compare the distance value to a set range, and a signaling mechanism operably connected to the microprocessor, said signaling mechanism for indicating when the distance value is within the desired range;
- measuring, using the accelerometer, an acceleration signal generated by the compression monitor during chest compressions;
- converting, using the processor, the acceleration signal into a chest compression displacement signal corresponding to the distance the chest is compressed by the administration of CPR, without reference to a signal derived from a source external to the module;
- wherein the processor is programmed to account for the effects, on the chest compression displacement signal, of accelerations that are caused by forces other than those created by the administration of CPR, whereby the processor is capable of determining the chest compression displacement signal by processing the acceleration signal;
- providing a signal corresponding to the distance value indicative of the displacement of the CPR recipient's chest.

19. The method according to claim 18, further comprising the steps of:
- signaling, using a signaling mechanism operably connected to the processor, when the linear displacement signal is within a predetermined range.

20. The method according to claim 18, further comprising the steps of:
- providing an automated constricting device and controlling said automated constricting device based on the signal corresponding to the distance value indicative of the displacement of the CPR recipient's chest.

* * * * *